United States Patent
Plutzky et al.

(10) Patent No.: US 6,869,603 B2
(45) Date of Patent: Mar. 22, 2005

(54) LIPOPROTEIN LIPASE AND LIPOPROTEIN LIPASE ACTIVATORS IN THE TREATMENT OF INFLAMMATORY CONDITIONS

(75) Inventors: Jorge Plutzky, Brookline, MA (US); Ouliana Ziouzenkova, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 173 days.

(21) Appl. No.: 10/289,203

(22) Filed: Nov. 7, 2002

(65) Prior Publication Data

US 2003/0129216 A1 Jul. 10, 2003

Related U.S. Application Data

(60) Provisional application No. 60/331,124, filed on Nov. 8, 2001.

(51) Int. Cl.$^7$ .................................................. A61K 38/46
(52) U.S. Cl. ........................ 424/94.6; 424/522; 424/725
(58) Field of Search ............................... 424/94.6, 522, 424/725

(56) References Cited

U.S. PATENT DOCUMENTS

| | | | |
|---|---|---|---|
| 4,701,322 A | 10/1987 | Dixon et al. | 424/70 |
| 4,707,354 A | 11/1987 | Garlen et al. | 424/47 |
| 4,760,095 A | 7/1988 | Djerassi et al. | 514/847 |
| 4,784,849 A | 11/1988 | Tutsky | 424/73 |
| 5,219,558 A | 6/1993 | Woodin, Jr. et al. | 424/59 |
| 5,256,404 A | 10/1993 | Martino et al. | 424/59 |
| 5,310,556 A | 5/1994 | Ziegler | 424/401 |
| 5,463,092 A | 10/1995 | Hostetler et al. | 554/40 |
| 5,494,657 A | 2/1996 | Swenson | 424/59 |
| 5,665,379 A | 9/1997 | Hërslof et al. | 424/450 |
| 5,981,586 A | 11/1999 | Pershadsingh | 514/543 |
| 6,028,109 A | 2/2000 | Willson | 514/567 |
| 6,060,515 A | 5/2000 | Elias et al. | 514/560 |
| 6,267,985 B1 | 7/2001 | Chen et al. | 424/451 |

OTHER PUBLICATIONS

Bardot, et al., "PPAR–RXR Heterodimer Activates a Peroxisome Proliferator Response Element Upstream of the Bifunctional Enzyme Gene," *Biochem. Biophys. Res. Comm.* 192:37–45 (1993).

Göttlicher, et al., "Fatty Acids Activate a Chimera of the Clofibric Acid–Activated Receptor and the Glucocorticoid Receptor," *Proc. Natl. Acad. Sci. USA* 89:4653–4657 (1992).

Issemann, et al., "Activation of a Member of the Steroid Hormone Receptor Superfamily by Peroxisome Proliferators," *Nature* 347:645–650 (1990).

Marcus, et al., "Diverse Peroxisome Proliferator–Activated Receptors Bind to the Peroxisome Proliferator–Responsive Elements of the Rat Hydratase/Dehydrogenase and Fatty acyl–CoA Oxidase Genes but Differentially Induce Expression," *Proc. Natl. Acad. Sci. USA* 90:5723–5727 (1993).

Muerhoff, et al., "The Peroxisome Proliferator–Activated Receptor Mediates the Induction of CYP4A6, a Cytochrome P450 Fatty Acid ω–Hydroxylase, by Clofibric Acid," *J. Bio. Chem.* 267:19051–19053 (1992).

Reddy, et al., "Carcinogenesis by Hepatic Peroxisome Proliferators: Evaluation of the Risk of Hypolipidemic Drugs and Industrial Plasticizers to Humans," *Crit. Rev. Toxicol.* 12:1–58 (1983).

Tugwood, et al., "The Mouse Peroxisome Proliferator Activated Receptor Recognizes a Response Element in the 5' Flanking Sequence of the Rat Acyl CoA Oxidase Gene," *EMBO J.* 11:433–439 (1992).

*Primary Examiner*—Jean C. Witz
(74) *Attorney, Agent, or Firm*—Michael A. Sanzo; Fitch, Even, Tabin & Flannery

(57) ABSTRACT

The present invention is directed to compositions which include the enzyme lipoprotein lipase. These compositions may be applied topically to the skin of a person to prevent dryness or treat inflammation. In addition, the invention is directed to the use of fibrates to enhance the activity of lipoprotein lipase. The fibrates may be used orally to treat inflammation or enhance metabolic energy production.

18 Claims, No Drawings

LIPOPROTEIN LIPASE AND LIPOPROTEIN LIPASE ACTIVATORS IN THE TREATMENT OF INFLAMMATORY CONDITIONS

CROSS REFERENCE TO RELATED APPLICATION

The present application claims the benefit of U.S. provisional application No. 60/331,124, filed on Nov. 8, 2001.

FIELD OF THE INVENTION

The present invention is directed to methods and compositions involving the activation of PPARα by either the enzyme lipoprotein lipase (LPL) or by the lipolytic product monoacylglycerol (MAG). It includes topical compositions in which LPL acts on lipophylic substrates to activate PPARα and thereby promote subsequent PPARα-mediated effects. It also includes therapeutic methods in which these compositions are used and therapeutic methods in which the expression levels of lipoprotein lipase is enhanced using fibrates. In addition, the invention is directed to the use of 14'apo-carotenal as an inhibitor of PPARα activity.

BACKGROUND OF THE INVENTION

The peroxisome proliferator-activated receptors act as nuclear transcription factors and occur in three different forms, PPAR-alpha, PPAR-delta and PPAR-gamma. When activated, these receptors regulate the expression of genes involved in a variety of metabolic pathways. PPARα-regulated target genes are centrally involved in the metabolism of fatty acids. Specific PPARα effects include an increase in fatty acid oxidation in peroxisomes and mitochondria. Additional evidence indicates that PPARα activation leads to a variety of anti-inflammatory effects. Known activators include fibrates, in use clinically, as well as herbicides and phthalate plasticizers (Reddy, et al., *Crit. Rev. Toxicol.* 12:1–58 (1983)).

The PPAR-alpha receptor has been isolated and is known to be activated by fatty acids (Isseman, et al., *Nature* 347:645–650 (1990); Gottlicher, et al., *Proc. Nat'l Acid. Sci. USA* 89:4653–4657 (1992); Tugwood, et al., *EMBO J.* 11:433–439 (1992); Bardot, et al., *Biochem. Biophys. Res. Comm.* 192:37–45 (1993); Muerhoff, et al., *J. Biol. Chem.* 267:19051–19053 (1992); Marcus, et al., *Proc. Nat'l Acid. Sci. USA* 90:5723–5727 (1993)). There have been suggestions that activators of this receptor may be useful in treating skin conditions (U.S. Pat. No. 6,060,515) and obesity (U.S. Pat. No. 6,028,109). In addition, at least one report has suggested that activators of the gamma form of PPAR may be useful in treating inflammatory skin conditions (U.S. Pat. No. 5,981,586). A better understanding of the way in which the PPAR receptors are activated, especially in terms of endogenous pathways, may lead to new and better approaches to therapy.

SUMMARY OF THE INVENTION

The present invention is based upon the discovery that the enzyme, lipoprotein lipase, acts upon its lipid substrates to produce free fatty acids and monoacylglycerols (MAG) and that these enzymatic products can activate peroxisome proliferation activating receptors (PPAR). PPAR-alpha receptors are preferentially activated and the gamma and delta forms of the receptor are activated to a lesser extent. Since it is known that the activation of PPAR-alpha enhances energy production in cells and alleviates inflammatory conditions, this discovery has therapeutic importance.

Of particular interest is the use of lipoprotein lipase in the treatment of inflammatory conditions of the skin such as psoriasis or sunburn. Interaction of the enzyme with substrates of monoglycerides, diglycerides or triglycerides leads to the generation of free fatty acid and MAG ligands and to the subsequent activation of the PPAR-alpha receptor. The major source of fatty acids from plant and animal origin are triglycerides, lipid particles consisting of three fatty acids esterified to a glycerol backbone. Triglycerides represent the most common natural store of stable fatty acids esters. Free fatty acids represent lipophylic compounds that have limited permeability through the skin barrier. These fatty acid compounds, when in their free form, rapidly undergo esterification, oxidation and other reactions that reduce or eliminate their effectiveness, and induce wide array of separate and likely competing biologic effects, including pro-inflammatory reactions. The generation of these fatty acid compounds through LPL immediately before their uptake by the skin circumvents such modifications while still leading to activation of PPAR pathways. Thus, one important feature of the present invention is that enzyme and substrate are not combined until immediately before compositions are applied. By keeping these components separate until the time of therapy, enzyme activity can be better maintained and free fatty acids and MAG are made available to cells for PPARα activation.

In its first aspect, the invention is directed to a kit which has a first container with lipoprotein lipase in a stabilized form, and a second container with a topical composition for application to the skin (including the scalp) of a patient. Stabilization of enzyme can be accomplished using methods well known in the art such as maintaining a relatively high protein concentration (e.g., by the addition of a carrier protein such as albumin), and the inclusion of antioxidants, antiproteases or other agents known to preserve enzymatic activity (e.g., glycerol). In a preferred method, the enzyme is stabilized by providing it in the form of a lyophilized powder.

The topical composition in the second container must contain a substrate that can be acted upon by the lipoprotein lipase. Thus, it must include monoglycerides, diglycerides, or, preferably, triglycerides. The free fatty acids and MAG generated by the lipoprotein lipase enzyme are able to reduce the dryness of skin or hair follicles, improve tissue elasticity, and prevent conditions such as dandruff.

In general, the kit described above will contain between 1 and 10,000 units of lipoprotein lipase and more typically between 2 and 500 units. Topical compositions will typically be in the form of a cream, lotion, lipstick, emulsion, conditioner or gel and comprise one or more polymers, emulsifiers or moisturizers. Other components that will typically be present include fatty acids, lipophylic vitamins, phospholipids and antioxidants. Kits may also include agents that induce endogenous lipoprotein lipase such as fibrates.

In another aspect, the invention is directed to a method of treating human skin to alleviate or prevent dryness, inflammation or irritation. The method involves mixing a topical skin composition containing monoglycerides, diglycerides or triglycerides with enzymatically active lipoprotein lipase. The enzyme should be present in the final mixture at a concentration of between 0.5 and 500 units per ml and, more typically, at between 1 and 200 units per ml. After mixing has been completed, the preparation should be applied to skin within a period of two hours. Preferably it should be applied within thirty minutes and, more preferably, within five minutes. Compositions may be used in the treatment of psoriasis, sunburn or other inflammatory conditions and may contain any of the agents described above including polymers, emulsifiers, moisturizers, fatty acids, lipophylic vitamins, phospholipids, antioxidants, fibrates or steroids. Stabilization of the enzyme is preferably achieved by providing it in the form of a lyophilized powder.

In another aspect, the invention is directed to the use of monoacylglycerols alone as PPAR-α activators. Thus, these agents may be used in the treatment of human skin or for other targets influenced by PPAR-α activation, for example dyslipidemia with increased triglycerides and lower HDL. Delivery of the monoacylglycerols can be achieved in a variety of ways, including intravenous administration.

The invention also includes methods that are based upon the discovery that PPAR-α activation leads to increases in the levels of lipoprotein lipase. This is relevant for PPAR-α activating fibrates currently in clinical use, as well as for other means of activating PPAR-α, such as the LPL and MAG activities described above. The effect is also relevant to future molecules, either synthetic or naturally-occurring, that are found to be PPAR-α activators. The application of these discoveries regarding LPL and PPAR-α will be especially relevant in areas in which these two pathways are centrally involved, namely inflammation and energy use. Fibrates may be used to treat inflammatory conditions, either directly, or through the indirect induction of LPL. Thus, fibrates themselves, or the production of PPAR-α activators through LPL, represent a mechanism for generating anti-inflammatory activity.

LPL plays an important role in providing energy by the liberation of fatty acids for PPARα activation as well as for subsequent beta-oxidation in mitochondria. The involvement of PPAR-α and LPL in energy metabolism suggests that fibrates and other PPAR-α activators can be used to stimulate the metabolic production of energy in an individual. Thus, the activators of PPAR-α may be useful as a component of foods or drinks for use after energy expenditure, or in patients needing additional energy sources, e.g., patients recovering from surgery, burn victims, etc. In addition, PPAR-α activators may be used in topical preparations to provide a source of energy. In the case of fibrates, sufficient compound should be present in compositions to provide an individual with between 20 mg and 2 grams. These agents can be used in topical preparations to increase effectiveness or, alternatively, may be orally administered to a patient as a treatment for conditions known to respond to PPAR-alpha activation.

In another aspect, the invention is directed at use of 14' apocarotenal as an inhibitor of both PPAR-α and of the retinoid X receptor (RXR). In addition to being useful as a research tool in in vitro studies of PPAR-α and RXR, this compound is also beneficial in certain clinical pathologic situations in which inhibiting PPAR-α activation is desirable. For example, the compound may be used to decrease lipid oxidation in certain pathological situations such as those associated with high blood glucose levels (e.g., in patients with insulin resistance). 14'apocarotenal may also be used in situations where inhibition of beta oxidation has been shown to be of clinical benefit, as with etomoxir-mediated inhibition of fatty acid transport as an intervention in acute cardiac ischemia and possibly insulin resistance.

DETAILED DESCRIPTION OF THE INVENTION

Fatty acids and MAG generated via LPL have been found to preferentially activate the PPAR-alpha receptor. The receptor then induces the expression of genes that enhance metabolic energy production and that lead to a reduction in inflammation. Free fatty acids generated by LPL on the cell surface are lipophylic in nature and are thus absorbed by cells and skin. In contrast, free fatty acids, when added alone, require the presence of a solubilizing agent such as ethanol, which can lead to dryness of the skin. Furthermore, the addition of free fatty acids alone (i.e., not generated through LPL as described herein) may be deleterious due to a variety of effects, including the stimulation of pro-inflammatory responses. Thus, PPAR-α activators generated through the LPL approach are especially well-suited for the treatment of inflammatory skin conditions such as psoriasis or sunburn. The enzymatically generated fatty acids also serve as moisturizing agents and can be used in skin lotions to alleviate dryness or in shampoos as a treatment for dandruff.

The PPAR-α activators of the present invention are generated by the enzymatic action of lipoprotein lipase on a monoglyceride, diglyceride or triglyceride. One essential feature of the invention is that the enzyme must be active and must have substrate to act upon either immediately before, or during, the time in which a preparation is in contact with a person's skin. This can best be achieved by keeping the enzyme separate from the substrate composition and mixing the two together immediately before a preparation is used.

Lipoprotein lipase is commercially available and methods for its production are well known in the art. It may be stabilized by any of the standard methods known in the art such as maintaining it in a buffer containing antioxidants, antiproteases, carrier proteins (e.g., albumin at a concentration of 1 mg per ml or higher) or by including other agents known to be effective in maintaining activity, e.g., glycerol or sucrose. In a preferred method, the enzyme is stabilized by providing it in the form of a lyophilized powder which may optionally contain other components or proteins.

The LPL enzyme is provided as part of a kit which also contains a lotion, cream, gel or emulsion suitable for topical application to the skin of an individual. The most essential feature of the topical composition is that it must contain monoglycerides, diglycerides or, preferably, triglycerides. Triglycerides are a major component in many readily available oils, any of which are suitable for use in the present invention, and methods for formulating topical compositions in which they are present are well known in the art (see e.g. U.S. Pat. No. 6,267,985). Examples of oils that may be used include canola oil, castor oil, coconut oil, corn oil, cottonseed oil, palm oil, peanut oil, soybean oil, olive oil, safflower oil, as well as certain sources of animal fat, e.g., marine mammals. If desired, triglycerides may also be added to preparations in a purified form.

Exemplary formulations of creams and lotions suitable for use in the present invention are disclosed in U.S. Pat. No. 4,707,354; U.S. Pat. No. 4,760,095; U.S. Pat. No. 5,494,657; U.S. Pat. No. 4,784,849; U.S. Pat. No. 4,701,322; U.S. Pat. No. 5,256,404; U.S. Pat. No. 5,219,558; and U.S. Pat. No. 5,310,556. Any other type of cream, gel, or lotion known to be suitable for application to the skin of a patient may also be used. These compositions will typically contain polymers, emulsifiers and/or moisturizing agents such as petrolatum, rose hips oil, borage oil, or jojoba oil. Compositions may also include nutrients or lipophylic vitamins such as vitamin A and vitamin E. Other components that may be present include fragrances, humectants, sunscreen agents, antiseptics and preservatives. Although not critical to the invention, as a general rule, it would be expected that a composition might contain up to 30% moisturizer with most of the rest of the composition being comprised of oil, water, emulsifier, and small amounts of additional agents such as vitamins (less than 1%). Conditioners or shampoos for use on the scalp of a patient may also be made using formulations well known in the art.

Kits having separate containers of topical skin composition and enzyme should also have instructions indicating that the components should be mixed before use and applied to either the skin or scalp of an individual. The method of combining active enzyme with a composition containing its substrate and then applying it in this manner is part of the invention. In addition, agents that enhance the activity of lipoprotein lipase may be included in kits or separately administered to individuals. In this connection, it has been found that fibrates are effective when administered. Examples of fibrates that may be used in oral dosages are as follows: bezafibrate: 200 mg two or three times a day; ciprofibrate: 100 mg per day; clofibrate: 1.5–2 grams per day in 2–4 doses; fenofibrate: 200 mg per day; and gemfibrozil: 600 mg, twice a day. All of these fibrates are presently on the market.

In addition to being administered in a tablet or capsule for the treatment of an inflammatory condition, fibrates may be included as part of a solid or liquid nutritional supplement. For example, fibrates may be included in a liquid that is ingested to bolster the energy of an individual. The concentrations described above may be used to provide guidance concerning the amount that should be present in nutritional compositions. If used as part of a topical preparation, it is expected that somewhat lower concentrations of fibrate will be present. Thus, a topical composition might contain between 0.1 and 1 mg per ml of fibrate.

EXAMPLES

Example 1

This study demonstrates that LPL acts on triglyceride-rich lipoproteins (TG-LP) to generate endogenous PPAR-alpha ligands.

A. Materials and Methods

Reagents: All reagents and media, unless otherwise indicated, were purchased from Sigma, St Louis, Mo. or BioWittaker, Md., respectively. All media contained fungizone/penicillin/streptomycin. Fenofibric acid was a gift from Laboratories Fournier, Daix, France.

Animals: PPAR-alpha$^{+/+}$ (129S3/SvImJ) mice were obtained from Jackson Laboratories (Bar Harbor, Me.). PPAR-alpha$^{-/-}$ mice were a gift from NIH. Mice overexpressing LPL specifically in cardiac and skeletal muscle were crossbred to homogeneity with PPAR-alpha$^{-/-}$ to obtain animals heterozygous for the LPL transgene.

Cell Culture: Circulating human monocytes were isolated from healthy volunteers. Differentiated cells (day 7–10) were treated in M199 medium. Peritoneal Mφ were isolated after 5% thioglycollate broth injection into 2–6 month old PPAR-alpha$^{+/+}$ and PPAR-alpha$^{-/-}$ mice. Mφ were cultured in 10% FCS/DMEM 24 h prior to stimulation. HepG2 cells (ATCC, Manassas, Va.) were cultured in 10% FCS/DMEM.

Lipoprotein isolation: Lipoproteins were isolated using gradient ultracentrifugation of human plasma pooled from at least 6 healthy donors. Cholesterol, TG, FFA (Hoffmann-La Roche, Basel, Switzerland), and protein (Pierce, Rockford, Ill.) content was measured by enzymatic assay. For labeling, VLDL was incubated for 10 h at 23° C. with 1,1'-dioctadecyl-3,3,3',3'-tetramethylindocarbocyanine perchlorate (DiI), final concentration 500 ng DiI/mg VLDL.

RNA analysis: Total cell RNA was isolated using RNAEasy kit (Qiagen, Valencia, Calif.), separated using a 1% agarose gel, transferred to a Hydrobone membrane (Amersham, Piscataway, N.J.) and Northern blotting was then performed. cDNA probes for LPL and ACO were obtained from ATCC (Manassas, Va.).

Transient transfection: Transient transfection was carried out in 24-well plates at 2.3×10$^4$ primary bovine aortic EC (passage 3–6) per well using Superfect (Qiagen) or Fugene (F. Hoffmann-La Roche). PCMX-β-galactosidase expression vector was used for transfection control. LPL and LPL mutant expression vectors have been previously characterized. Luciferase (Pharmingen, San Diego, Calif.) and P-galactosidase activity were measured according to manufacturer's protocols.

Immunohistochemistry: Acetone-fixed mouse PPAR-alpha$^{+/+}$ and PPAR-alpha$^{-/-}$ peritoneal Mφ cultures were incubated with rabbit anti-PMP-70 antibody (1:200, Affinity Bioreagents, Golden, Colo.) and visualized by FITC-conjugated streptavidin. Similar staining of frozen peripheral muscle sections was performed using PMP-70 antibody and secondary TRITC-conjugated antibody (R0156, Dako, Denmark) and analyzed using laser-scanning confocal microscopy (MRC 600, Biorad, Richmond, Calif.).

B. Results

LPL lipolysis of TG-LP generates PPARα ligands: We tested if LPL generates endogenous PPAR-alpha ligands from TG-LP by analyzing activation of chimeric PPAR-alpha-ligand binding domain (LBD) constructs in yeast GAL4 assays. Transfection was performed in primary bovine endothelial cells which do not express LPL. While lipoproteins alone failed to activate the PPAR-alpha-LBD in the presence of recombinant LPL, these lipoproteins significantly induced PPAR-alpha activation in a concentration-dependent manner. Half-maximal values (EC$_{50}$) for PPAR-alpha activation were 1.5, 5, and 20 μg protein/ml for VLDL, LDL and HDL. Maximal induction was highest for VLDL (21 fold), followed by LDL (14 fold) and HDL (7 fold).

To examine the specificity of PPAR ligands generated by VLDL and recombinant LPL treatment (VLDL/LPL), experiments were repeated using chimeric LBD/GAL4 constructs for PPAR-gamma, PPAR-delta, and PPAR-alpha. Responses were compared to their respective high affinity PPAR ligands and a GAL4-control plasmid. In the absence of LPL, VLDL failed to induce any PPAR-LBD response. LPL/VLDL most potently activated PPAR-alpha-LBD, followed by PPAR-delta, and PPAR-gamma. GAL4 alone was unchanged. This suggests that, in the presence of LPL, VLDL preferentially activates PPAR-alpha.

LPL lipolysis of TG-LP activates PPARα-regulated genes: We tested if activation of PPAR-alpha by VLDL/LPL induced expression of an established PPAR-alpha target gene, acyl-coenzymeA-oxidase (ACO). It was found that LPL treatment induced ACO mRNA in a time and VLDL concentration-dependent manner in both HepG2 and primary human macrophages. While LPL had no effect, VLDL alone induced ACO. This was probably due to basal lipase expression as suggested by the observation that tetrahydrolipstatin inhibited this VLDL response in HepG2. In vivo, increased ACO expression has been shown in LPL-overexpressing mice. Consistent with reports of PPAR-alpha regulation of LPL expression, VLDL/LPL also induced LPL expression in these cells.

LPL lipolysis of TG-LP induces peroxisome proliferation and PPAR-alpha-dependent target genes: To demonstrate that the observed VLDL/LPL effects were dependent on the presence of PPAR-alpha, we turned to a genetic loss of function model, the PPAR-alpha$^{-/-}$ mouse. In rodents, the hallmark of PPAR-alpha activation is peroxisomal proliferation in response to synthetic agonists. Using peroxisomal membrane protein-70 (PMP-70) immunohistochemistry, we found that LPL/VLDL induced peroxisomal proliferation in mouse peritoneal Mφ to at least the same extent as the synthetic PPAR-alpha agonist WY14643. These responses were absent in PPARα$^{-/-}$ Mφ.

Consistent with this, VLDL/LPL treatment of mouse peritoneal Mφ also significantly induces mRNA expression of PPAR-alpha target genes ACO and LPL, a response decreased significantly in PPAR-alpha$^{-/-}$ Mφ. Basal expression of ACO and LPL is consistent with the known regulation of these genes by other pathways. This indicates that a positive feedback loop for LPL-expression through VLDL/LPL is regulated via PPAR-alpha-dependent mechanisms.

To address LPL effects in vivo, peroxisome proliferation was studied in the skeletal muscle of LPL-overexpressing transgenic mice bred to PPAR-alpha$^{-/-}$ or PPAR-alpha$^{+/+}$ mice. The increased PMP-70 positive granules observed in LPL overexpressing/PPAR-alpha$^{+/+}$ mice on regular chow were absent in LPL-overexpressing/PPAR-alpha$^{-/-}$ mice. Thus, increased LPL expression in vivo induces peroxisome proliferation in a PPAR-alpha-dependent manner.

Activation of PPARα via LPL is dependent on intact enzymatic activity: To address the mechanisms through which LPL/VLDL activates PPAR-alpha, we considered if PPAR-alpha-LBD activation depended on the enzymatic activity of LPL, or alternatively on the bridging effect of LPL between proteoglycans and lipoprotein receptors which promotes lipoprotein uptake. PPAR-alpha-LBD activation experiments were performed after altering bridging responses by overexpressing the LDL receptor; adding heparin and heparinase which may affect receptor-mediated uptake; or the actin inhibitor cyclochalasin, which impairs post-receptor endosomal processing. None of these treatments had any effect. PPAR-alpha activation was not due to decreased lipid uptake as shown by uptake of DiI-labeled VLDL in the presence and absence of LPL. Abundant labeled-lipid was present intracellularly even in the absence of LPL. Thus, VLDL uptake probably is not responsible for PPAR-alpha-LBD activation by VLDL/LPL.

In contrast, addition of heat-inactivated LPL or transfection of a catalytically-inactive LPL failed to induce PPAR-alpha-LBD activation. Furthermore, the lipase inhibitor tetrahydrolipstatin inhibited LPL-mediated PPAR-alpha-LBD activation in a dose-dependent fashion. Thus, multiple lines of evidence indicate that LPL generation of PPAR-alpha activators from VLDL by LPL depends on its intact catalytic activity.

Monoacylglycerol represents a novel group of PPARα activators: We asked if PPAR-alpha activation through the hydrolysis of LP extended to other lipolytic enzymes which generate FFA, known PPAR-alpha activators. We tested PPAR-alpha-LBD activation after phospholipase A$_2$ (PLA$_2$), phospholipase D (PLD), and phospholipase C (PLC) treatment of different LP. All these enzymes lacked significant PPAR-alpha-LBD activity despite significant FFA release from LP. These results do not exclude FFA activation of PPAR-alpha, but suggest the role of specific enzymatic pathways, or their products, in these responses.

LPL catalyzes primarily the hydrolysis of TG producing free FA (FFA) and monoacylglycerols (MAG), a glycerol backbone with a single fatty acid side-chain. We considered if MAG, as a specific LPL lipolytic product, contributes to PPAR-alpha-LBD activation. It was found that MAG activates PPAR-alpha-LBD with the highest maximal inductions occurring with saturated 14:0 or 16:0 MAG and MAG containing linoleic acid (18:2). The EC50 of MAG containing a defined FA were similar or higher than that of the corresponding free FA alone. Thus, products of LPL-catalyzed hydrolysis, but not diacylglycerols (DAG), are significant activators of PPAR-alpha. TG content in the LP tested were VLDL>>LDL>HDL (328, 52, 28 mg TG/dL) and correspond to EC50 values of ~20 μM, ~2 μM and ~3 μM TG, respectively. Assuming complete lipolysis of 20 μM VLDL, this will produce ~20 μLM MAG and a total of ~40 μM FFA, indicating TG hydrolysis of VLDL as a feasible ligand source accounting for PPARα activation.

C. Discussion

The results above link LPL-mediated catabolism of TG-LP to activation of the nuclear receptor PPAR-alpha and to its distal transcriptional effects. LPL treatment of TG-LP at physiologic concentrations induces the expression of PPAR-alpha target genes, including ACO and LPL itself. These responses depend on intact LPL enzymatic activity. In vivo, gain of function experiments with transgenic overexpression of LPL show increased peroxisome proliferation, a biologic marker of PPAR-alpha activation in mice. The loss of PPARα function in mice abrogates LPL-mediated peroxisome proliferation and target gene induction. This data establishes LPL-mediated hydrolysis of TG-LP as an endogenous pathway for PPAR-alpha activation under physiologic conditions, with evidence for a positive feedback loop promoting further TG-LP metabolism.

Example 2

Low density lipoprotein (LDL) is a major carrier of cholesterol in circulation. It represents a heterogeneous population of particles and includes an in vivo modified subfraction with a higher electronegative charge (LDL−). High LDL− levels have been found in diseases associated with accelerated atherosclerosis, i.e., familial hypercholesterolemia, diabetes, and in patients undergoing hemodialysis. This study shows that lipoprotein lipase (LPL) generates PPAR-alpha ligands utilizing LDL−, an effect countering pro-inflammatory VCAM-1 expression mediated by LDL− and TNFα.

A. Materials and Methods

Reagents: Recombinant LPL and WY 14643 were purchased from Sigma, St Louis. Fenofibric acid was a generous gift from Furnier.

LDL isolation: Plasma from healthy donors was subjected to hemoglobin-mediated oxidation. LDL was isolated from oxidized and non-oxidized plasma and designated as LDL and LDL− respectively. Cholesterol and triglyceride content was measured by enzymatic kits (Sigma, St Louis). Electrophoretic mobility was determined using LipoGel (Beckman). Anion exchange chromatography was utilized to purify LDL− fraction or to measure LDL− content.

Cell Culture: Human endothelial cells were isolated from umbilical veins and cultured in M199 medium (BioWittaker) containing penicillin/streptomycin, Fungozom, ECGF and 5% fetal calf serum. Cells from passage 3 to 5 were used for experiments. Cells were pretreated with 100 uM fenofibric acid or WY 14643 for 24 h and with LDL species/LPL for 1 h prior to addition of 50 ng/ml TNFα. Subsequent duration of incubations varied. Prior to any procedure cells were washed with ice-cold PBS.

RNA analysis: Total cell RNA was isolated using RNA easy kit (Qiagen, Germany). RNA was separated using 1% agarose gels and transferred to Hydrobone membranes. Northern blot analyses were then performed.

Protein Extraction, Western blot, EMSA: Analyses were performed in cells harvested in PBS lysis buffer containing freshly added 1 mM phenylmethylsulphonyl fluoride on ice. Cell homogenates were collected by centrifugation at 4° C. Nuclear extracts were isolated and protein concentration was determined using bicinchonic acid kit (Pierce). Equal amounts of protein were subjected to electrophoresis on 12% polyacrylamide gels under reducing conditions (b-mercaptoethanol). Proteins were transferred onto polysulphone membranes using semi-dry transfer (1.5 h, 16V). Non-specific binding sites were blocked 1 h with 5% nonfat milk in TBST (20 mM Tris, 55 mM NaCl, 0.1% Tween 20) and then membranes were incubated with monoclonal antibody against PPAR-alpha. Signals were visualize by chemiluminescence (NEN, USA) after incubation with secondary horseradish peroxidase-conjugated antibody. For EMSA nuclear extracts were obtained from HUVEC.

Cell surface ELISA assays were preformed in 96-well plates on confluent monolayers of HUVEC. Treated cells were maintained on ice for 10 minutes, washed with cold PBS and incubated with monoclonal antibodies raised against human VCAM-1. VCAM-1 expression was visualized using alkaline phosphate secondary antibody and measured at 4 mm.

Transient transfection: Transient transfection was carried out in primary (passage 3 to 6) bovine aortic endothelial cells using the Superfect method (Qiagen, Germany) according to manufacturer's directions. Briefly, cells were plated in 24-well plates at $2.3 \times 10^4$ cells per well in DMEM containing 10% fetal calf serum. After 16 h of growth, cells were washed with HBSS and transfected with medium containing Superfect/DNA (ratio 5.5/1) for 4 hours or with FuGene (1.5/1) overnight. Reporter construct pUASx4-TK-luc, chimeric human PPAR-alpha-LBD constructs, PPAR-alpha and LDL receptor (LDLr) overexpression vectors, and the VCAM-1 promoter-luc, have been described previously. A PCMX-B-galactosidase expression vector was used as a transfection control. Cells were maintained overnight in medium, followed by treatment with compounds for 10 hrs in DMEM medium containing 1% FCS (for PPAR-alpha-LBD constructs) and 1% Nutridoma SP (for VCAM-1 promoter studies). Cells lysed in buffer (Pharmingen) were assayed for luciferase activity using a reported assay system (Pharmingen) according to the manufacturer's instructions. β-galactosidase activity was monitored at 540 nm using CRPTG (Boeringer Mannheim) as substrate.

B. Results

LDL− augments TNFα-mediated VCAM-1 expression: Surface expression of VCAM-1 was studied in HUVEC activated by TNFα. Cell stimulation with LDL− lead to approximately a two-fold increase in VCAM-1 expression. In presence of TNFα, VCAM-1 expression was increased 5-fold. This increase was further augmented by LDL− but not by native LDL. We had previously found that TNFa-dependent VCAM-1 expression is reduced in cells pretreated with ligands for PPAR-alpha. Here we found a 50% decrease in VCAM-1 expression induced by LDL− and TNFα but pretreated with PPAR-α agonists. Similarly, a dose-dependent elevation of VCAM-1 promoter induction was observed in transient transfection experiments in BoEC stimulated with LDL− and TNF-α. The VCAM-1 activation was reduced by two-fold in cells ectopically expressing human PPAR-alpha. Fenofibric acid markedly decreased LDL−/TNFα dependent VCAM-1 induction (40 and 60% in cells co-transfected with control or PPAR-alpha vectors, respectively).

LPL reduce LDL−/TNFα-mediated VCAM-1 expression: In the presence of LDL−, we observed a 70% and 50% increase in VCAM-1 expression measured by ELISA, above that mediated by TNFα alone or in combination with native LDL. The up-regulation of VCAM-1 by LDL− was decreased in presence of LPL in dose-dependent fashion. LPL does not affect the 5-fold increase in VCAM-1 expression mediated by TNFα. This effect depends on the ectopic expression of PPAR-alpha which significantly decreases both the increase in TNFα/LDL− dependent VCAM-1 expression and its down-regulation through LPL.

PPAR-alpha: It been shown previously that PPAR-alpha ligand-dependent decreases in VCAM-1 expression are essentially dependent on the down-regulation of binding activity of transcription factor NFKB. In the present study, it was found that, while LDL− further increases NFkB binding in TNFα-activated cells, this increase is abrogated in the presence of LPL. This effect was stronger then that mediated by fenofibric acid, a high affinity ligand for PPAR-alpha and abrogated in macrophages obtained from PPAR-α deficient mice. NFkB is a regulator of variety of proinflammatory genes.

LPL lipolysis of LDL− generates PPAR-alpha ligands: LPL mediates the hydrolysis of LDL−triglycerides to free FA and monoglycerol. The majority of FA found in LDL are low affinity ligands. We found that LPL generates specific PPAR-α ligands, with this evidence deriving from use of a yeast two hybrid In studied donors (n=10), the PPAR-alpha activation was higher in cells stimulated with LDL− compared to non-modified LDL. In fact LDL− stimulation was correlated with PPAR-alpha ligand binding domain (LBD) activation. LPL leads to marked activation of PPAR-alpha-LBD for LDL and LDL−. This effect was comparable to that caused by fenofibric acids. LPL activation of PPAR was specific for the PPAR-alpha isoform as compared to the PPAR-gamma isoform of a control GAL4 plasmid. The LPL effect on PPAR-alpha-LBD activation is dependent on the LDL and LDL− dose, reaching an activation plateau at approximately 5–10 ug/ml of LDL− species. LDL− leads to a significantly stronger PPAR-alpha maximum induction compared to LDL.

LPL/LDL− dependent activation of PPAR-alpha required the catalytic activity of LPL. Activation was inhibited by the natural LPL inhibitor ApoCIII and by antibody raised against lipase but not by antibody to the LDL receptor (LDLr). Heat inactivation or mutation of LPL reduced the LDL−/LPL activation of PPAR-alpha to the levels observed with LDL− alone. In contrast, incubation of LPL with LDL− for 30 minutes and subsequent degradation of the incubation mixture by ethanol lead to a similar PPAR-alpha activation in cells as that observed with intact LPL and LDL−. LPL-mediated generation of PPAR-alpha ligands appears to be unaffected by LDLr. LDL and LDL− activate PPAR-alpha-LBD to a similar extent in cells transiently transfected with control and LDLr-containing overexpression vectors. In contrast, LDLr expressing cells have marked upregulation of the VCAM-1 promoter. Thus, LPL-mediated lipolysis may represent a natural pathway for PPAR-alpha activation capable of countering proinflammatory NFkB activation and VCAM-1 expression.

C. Discussion

In this study it was found that the novel anti-inflammatory properties of LPL resulted in the inhibition of adhesion molecule expression (VCAM-1) activated by the LDL-subfraction and TNFα. Similar effects were observed with triglyceride-rich native VLDL. The liberation of free fatty acids and monoacylglycerols catalyzed by LPL can increase the intracellular level of PPAR-alpha ligands and thereby activate PPAR-alpha. We found that LPL-mediated catabolism of LDL and LDL− markedly increased PPAR-alpha ligand levels in a dose dependent manner with the approximate half induction concentration of 5 ug LDL protein/ml. The extent of PPAR-alpha-LBD activation was similar to that induced by 100 uM fenofibric acid. PPAR-alpha activation was dependent on the catalytic activity of LPL and was abolished in presence of ApoCIII, lipase antibody, or inactivated LPL.

Transfection experiments utilizing the LDL receptor vector showed that the LDL receptor markedly promotes activation of the VCAM-1 promoter but has no effect on the LPL-mediated activation of PPAR-alpha. Moreover, the bridging of LPL appears to be not essential for PPAR-alpha activation, because the LDL− and LPL mixture obtained during extracellular incubation and subsequent degradation with ethanol, induces a similar PPAR-alpha activation as LDL−/LPL directly introduced to cells. Thus, LPL-dependent lipolysis but not LDL receptor mediated uptake of LDL− generates PPAR-alpha ligands.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A kit comprising:
   (a) a container comprising the enzyme lipoprotein lipase in a stabilized form; and
   (b) a container comprising a topical composition for application to the skin of a human wherein said topical composition comprises monoglycerides, diglycerides or triglycerides of synthetic, plant, or animal origin.

2. The kit of claim 1, wherein said enzyme is present in an amount of 1–10,000 units.

3. The kit of claim 1, wherein said enzyme is present in an amount of 2–500 units.

4. The kit of claim 1, wherein said topical composition is a cream, lotion, emulsion, shampoo, conditioner or gel and comprises one or more polymers, antioxidants, emulsifiers or moisturizers.

5. The kit of claim 4, wherein said topical composition further comprises one or more components selected from the group consisting of: fatty acids; lipophylic vitamins; phospholipids; and antioxidants.

6. The kit of claim 1, wherein an agent enhancing the activity of said lipoprotein lipase is present in either the container comprising said enzyme or the container comprising said topical composition.

7. The kit of claim 1, further comprising a fibrate.

8. The kit of claim 7, wherein said fibrate is present in a container separate from said lipoprotein lipase and from said topical composition.

9. The kit of claim 1, wherein said enzyme is present as a lyophilized powder.

10. A method of treating human skin to alleviate or prevent dryness, loss of elasticity, inflammation or irritation, said method comprising:
    (a) mixing a topical skin composition with lipoprotein lipase, wherein:
        (i) said topical skin preparation comprises monoglycerides, diglycerides or triglycerides;
        (ii) said lipoprotein lipase is present in the mixture produced at a concentration of 0.5–500 units per ml;
    (b) topically applying the mixture of step (a) to said human skin, wherein application is performed within two hours of the time said topical composition and said lipoprotein lipase are mixed.

11. The method of claim 10, wherein said lipoprotein lipase is present in the mixture of step (a) at a concentration of 1–200 units per ml.

12. The method of claim 10, wherein the application of mixture to skin occurs within thirty minutes after mixing.

13. The method of claim 10, wherein the application of mixture to skin occurs within five minutes of mixing.

14. The method of claim 10, wherein said human skin is treated for psoriasis or sunburn.

15. The method of claim 10, wherein said topical composition is a cream, lotion, emulsion, or gel comprising one or more polymers, emulsifiers or moisturizers.

16. The method of claim 15, wherein said topical composition further comprises one or more components selected from the group consisting of: fatty acids; lipophylic vitamins; phospholipids; and antioxidants.

17. The method of claim 10, wherein the mixture of said lipoprotein lipase and said topical composition further comprises one or more fibrates.

18. The method of claim 10, wherein said lipoprotein lipase is in the form of a lyophilized powder prior to mixing.

* * * * *